United States Patent [19]

Nagai

[11] 4,178,795
[45] Dec. 18, 1979

[54] PLUGGING METER

[75] Inventor: Akinori Nagai, Higashi, Japan

[73] Assignee: Doryokuro Kakunenryo Kaihatsu Jigyodan, Tokyo, Japan

[21] Appl. No.: 831,678

[22] Filed: Sep. 8, 1977

[30] Foreign Application Priority Data

Sep. 22, 1976 [JP] Japan .............................. 51-113937

[51] Int. Cl.² ........................................... G01N 11/00
[52] U.S. Cl. ............................................... 73/61 LM
[58] Field of Search ................ 73/61 LM, 15 R, 17 R

[56] References Cited

U.S. PATENT DOCUMENTS

| | | | |
|---|---|---|---|
| 2,782,369 | 2/1957 | Werner et al. | 73/61 LM UX |
| 2,997,874 | 8/1961 | Billuris et al. | 73/61 LM |
| 3,200,637 | 8/1965 | Ballou et al. | 73/61 LM |
| 3,390,571 | 7/1968 | Roach et al. | 73/61 LM |
| 3,672,209 | 6/1972 | Roach et al. | 73/61 LM |

FOREIGN PATENT DOCUMENTS 37320  3/1967  Japan .................................. 73/61 LM

*Primary Examiner*—Richard C. Queisser
*Assistant Examiner*—Joseph W. Roskos
*Attorney, Agent, or Firm*—Wenderoth, Lind & Ponack

[57] ABSTRACT

A plugging meter for automatically measuring the impurity concentration in a liquid metal is designed to have parallel passages including a cooling passage provided with a plugging orifice and with a flow meter, and a by-pass passage connected in series to a main passage having another flow meter, so that the plugging points may be obtained from the outputs of both flow meters. The plugging meter has a program signal generator, a flow-rate ratio setter and a comparator, and is adapted to change the temperature of the plugging orifice in accordance with a predetermined pattern or gradient, by means of a signal representative of the temperature of plugging orifice and a flow-rate ratio signal obtained from the outputs of both flow meters. This plugging meter affords an automatic and accurate measurement of a multi-plugging phenomenon taking place at the plugging orifice.

7 Claims, 2 Drawing Figures

PLUGGING METER

BACKGROUND OF THE INVENTION

The present invention relates to a plugging meter for automatically measuring the density or concentration of impurities contained in a liquid metal such as liquid sodium and the like. More particularly, the present invention is concerned with a plugging meter capable of automatically and accurately observing a multi-plugging phenomenon taking place in a system composed of structural members of ferritic stainless steel and austenite stainless steel, such as a sodium-heated steam generator.

As is well known, liquid metals such as liquid sodium have a large heat-transfer coefficient, and remain in liquid phase to a sufficiently high temperature. In addition, they are less likely to be damaged by radioactive rays. For these reasons, the liquid metals are advantageously used as coolants for power sources which operate at a high temperature, such as a nuclear reactor and the like.

Impurities in liquid sodium (chiefly $Na_2O$, $NaOH$, $NaH$, $Na_2CO_3$ and the like) must be removed by a cold trap or the like, even when they are present in extremely small amounts, because they may cause corrosion and/or clogging of the sodium-carrying apparatus.

A plugging meter has been developed as a means for detecting the concentration or density of the impurities in liquid metals, and has been successfully used in managing the purity of liquid sodium.

However, the initial operating period of sodium loops or in sodium systems employing ferritic stainless steel, a multi-plugging phenomenon is often observed, which makes automatic measurement difficult.

The plugging meter has an orifice installed in the path of the liquid sodium, and makes use of a plugging of the orifice by the deposition of impurities which takes place as the temperature of the liquid sodium is lowered to a certain temperature. Thus, the concentration or density of the impurities can be determined by the reduction of flow rate, in relation to the temperature around the orifice.

All of the plugging meters proposed up to now are based on this principle, but have various constructions. The plugging meter which is most relevant to the present invention has a following construction.

A cooling passage provided with cooling equipment and a by-pass passage in combination therewith constitute parallel liquid sodium paths which are connected between an inlet pipe having a first flow meter and an outlet pipe.

The liquid sodium having entered the inlet pipe then flows through both the cooling passage and the by-pass passage, and then the parallel flows are formed and discharged through the outlet pipe. A plugging orifice section is provided in the cooling passage, near the downstream end or outlet port thereof. The orifice section is provided with a thermocouple for measuring the sodium temperature.

Also, the cooling passage has a second flow meter for measuring the sodium flow rate in the plugging orifice section. The output signals from above two flow meters are processed by a divider, which produces a signal representative of the ratio of the flow rates. The temperature of the orifice is controlled by means of a blower and an associated damper of the cooling equipment.

For manual measuring by this plugging meter, at first the blower is started and then the damper is gradually opened manually, while watching the temperature of the plugging orifice, so as to gradually lower the temperature. After a certain period of the constant flow-rate ratio signal, the plugging starts to take place, which can be detected by a decrease of the signal. In case of a double plugging pattern, at first a first plugging is observed and, after a subsequent temporary lull, a second plugging comes to be observed as the temperature is further lowered. The substances causing plugging, as well as their concentrations, can be determined from the respective plugging temperatures.

Then, the damper is fully closed and the fan is stopped to allow the temperature of the plugging orifice to rise. The temperature is then raised up to the starting temperature, for unplugging the orifice.

The plugging meter of the kind described can be controlled for an automatic measurement, when combined with a suitable automatic controller as described below.

Namely, an automatic controller is provided which performs a comparison of the input signal representative of the flow-rate ratio from the divider with a given value. Usually, this given value is selected to be a signal value equal to the flow-rate ratio exhibited when there is a slight deposition of the impurities at the plugging orifice. The automatic controller acts to increase the degree of opening of the damper to lower the temperature of the liquid sodium, so as to promote the deposition of the impurities, when the measured flow-rate ratio is greater than the given value, while, when the measured flow-rate ratio is smaller than the given value, the controller acts to increase the degree of opening of the damper, so that the sodium temperature will be raised to enhance the dissolution of the impurities.

Thus the controller serves to maintain an equilibrium of deposition and dissolution of impurities at the plugging orifice, and the sodium temperature at this state is detected as the plugging temperature.

It will be seen that the multi-plugging phenomenon can be detected by a manual measurement only by a very troublesome measuring operations. On the other hand, the automatic measurement system can perform the measurement for only one plugging substance. Further, in the latter case, the plugging temperature is difficult to establish when the plugging substance is one which is only slightly dissolved by the liquid sodium, so that the measurement is made difficult.

SUMMARY OF THE INVENTION

It is therefore an object of the invention to provide a plugging meter capable of automatically measuring the density or concentration of impurities in a liquid metal.

It is another object of the invention to provide a plugging meter capable of automatically measuring all of the multi-plugging substances at one time.

It is still another object of the invention to provide a plugging meter capable of automatically measuring temperatures for a multi-plugging phenomenon, as well as unplugging temperatures which heretofore could not be accurately measured by conventional measuring instruments.

According to the invention, there is provided a plugging meter comprising a piping system having a cooling passage provided with a plugging orifice and a flow meter and a by-pass passage by-passing said cooling passage, said plugging orifice having a temperature measuring means, said piping system consisting of the cooling and by-pass passages being connected to a main passage having another flow meter therein, a cooling system adapted to cause a change in the temperature of the liquid metal passing through said cooling passage, and a controlling system adapted to control said cooling system in accordance with signals delivered from said piping system.

The controlling system has a program signal generator adapted to generate a reference signal for elevating and lowering the orifice temperature on a predetermined gradient, a comparator adapted to compare the reference signal with the signal corresponding to the measured orifice temperature and to produce a signal representative of the difference which temperature difference signal controls the operation of the cooling system, and a flow-rate ratio setting device adapted to compare the flow-rate ratio signal with a desired value and to control the operation of the program signal generator in accordance with the flow rate ratio difference signal.

These and other objects, as well as advantageous features of the invention will become clear from the following description of the preferred embodiment taken in connection with the attached drawings.

DESCRIPTION OF THE PREFERRED EMBODIMENTS

Figure 1:
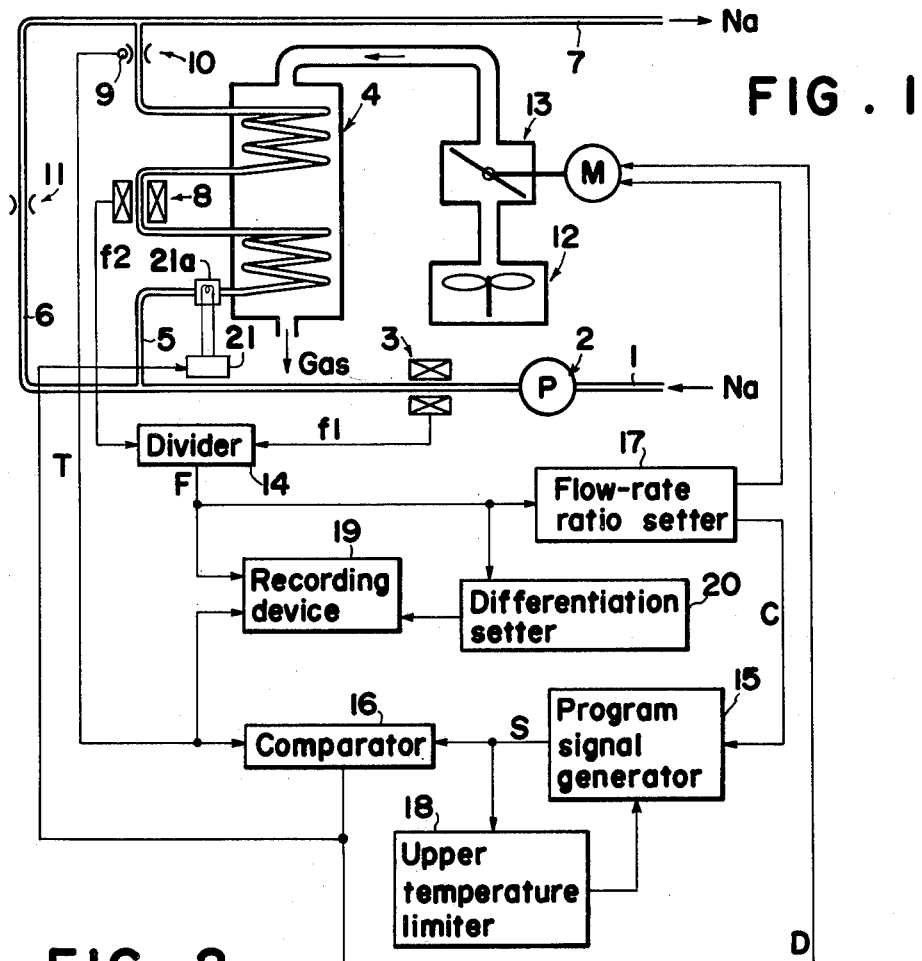
FIG. 1 is a schematic illustration of a plugging meter in accordance with the present invention, showing a block schematic diagram of an electronic controlling system in connection with a sodium flow piping system with a cooling system.

Referring at first to FIG. 1, a plugging meter embodying the present invention is shown to have a piping system through which liquid sodium flows, a temperature controlling system adapted to control the temperature of the liquid sodium passing through a cooling passage of the piping system, and an automatic measurement controlling system for controlling the temperature controlling system in accordance with various signals from the piping system.

The piping system has an inlet or main pipe 1 provided with an electromagnetic pump 2 and a first flow meter 3. The inlet pipe 1 is branched into a cooling passage 5 having a cooling system 4 and a by-pass passage 6 which are rejoined in to a common outlet or main pipe 7.

The cooling passage 5 is provided with a second flow meter 8 for measuring the flow rate of liquid sodium passing therethrough and a plugging orifice 10 equipped with a temperature sensor 9. The plugging orifice 10 is located in the vicinity of the outlet port of the cooler 4 provided for the cooling passage 5.

Any type of flow meter capable of obtaining electric signals representative of the flow rates of liquid sodium may be used for meters 3 and 8. Thus, an electromagnetic flow meter, an ultrasonic flow meter or other known flow meters can be used as the flow meters 3 and 8. Also, any known type of temperature sensor capable of providing an electric output signal representative of the sodium temperature may be used as the temperature sensor 9. Thus, a thermocouple, a thermoresistance or the like can be used as the temperature sensor 9.

The by-pass passage 6 is also provided with an orifice 11 for controlling the flow rate of the liquid sodium passing therethrough.

The cooler 4 is a forced ventilation type having a fan or blower 12 for delivering a cooling inert gas and a damper 13 adapted for adjusting the flow rate of the cooling gas.

The flow rate signals delivered from the first and the second flow meters 3 and 8 are processed by a divider 14 adapted for producing a flow-rate ratio signal F. The divider 14 may be a commercially available IC device.

The flow-rate ratio signal F is a signal representative of the ratio of the flow rate signal f2 of the second flow meter 8 (this signal represents the flow rate through the plugging orifice) to the flow rate signal f1 of the first flow meter 3 (this represents the total flow rate). That is, signal F corresponds to f2/f1.

The characteristic of the invention is in the automatic measurement controlling system described below.

The automatic measurement controlling system has a program signal generator 15 adapted to produce a reference signal S for elevating and lowering the temperature of the plugging orifice 10 with a predetermined temperature pattern or gradient.

As is well known, the program signal generator 15 is adapted to produce a voltage signal in accordance with a predetermined program. The program signal generator 15 incorporated in the controlling system of the invention provides an output voltage signal which changes with a constant ascending and descending gradient during a certain period of time. Preferably, the ascending and descending gradients are manually adjustable.

The reference signal S provided by this program signal generator 15 is delivered to a comparator 16, along with the temperature indicating signal T provided by the temperature sensor 9. The comparator 16 then compares the two signals with each other and produces a temperature difference signal D which is supplied to a damper driving motor M for opening and closing the damper 13. Thus, the motor M is controlled by the temperature difference signal D, for controlling the degree of opening of the damper 13.

The comparator 16 may be of a known type such as a PID controller adapted to receive cascade signals which is used in controlling systems.

The arrangement is such that the temperature difference signal D delivered from the comparator 16 is small when the reference signal S transmitted from the program signal generator 15 is greater than the temperature signal T transmitted from the temperature detector 9, so that the degree of opening of the damper is reduced to decrease the flow rate of the cooling gas supplied to the cooler 4, thereby to raise the temperature of the plugging orifice 10.

On the contrary, when the reference signal S is smaller than the temperature signal T, the level of the temperature difference signal produced by the comparator 16 is raised to make the degree of opening of the damper 13 larger, so as to increase the flow rate of the cooling gas supplied to the cooler 4, thereby to reduce the temperature of the plugging orifice 10. Thus, the plugging temperature is changed in accordance with the change in the reference signal supplied from the program signal generator 15.

The aforementioned flow-rate ratio signal F is then delivered to a flow-rate ratio setting device 17 which may be, for example, variable threshold level comparators constituted by use of OP-amps. The threshold can be manually set at any desired flow-rate-ratio, for example, by adjusting a potentiometer for adjusting the threshold.

The flow-rate ratio setter 17 performs a comparison of the settings with the aforementioned flow-rate ratio signal F, and transmits a control signal C representative of the difference between the flow rate ratios to the program signal generator 15 for controlling the latter. At the same time, the reference signal S is transmitted from the program signal generator 15 to an upper temperature limiter 18 which may consist, similarly to the aforementioned flow-rate ratio setter 17, of a level comparator comprising an OP-amp and having a variable threshold. The upper temperature limiter then compares the transmitted reference signal S with the pre-set upper limit temperature signal and produces a signal which represents whether the pre-set upper limit temperature has been reached. The program signal generator is also controlled by this output signal.

The temperature signal T, as well as the flow-rate ratio signal F, is delivered to and recorded by a recording device 19 having a marking means. The recording device 19 is capable of writing marks in accordance with signals transmitted from a differential setter 20 which consists of a combination of level comparators and a differentiation circuit. Thus, the flow-rate ratio signal is differentiated by the differentiation circuit, and the latter produces an output signal which is delivered to the level comparators. The level comparators then compare the signal with each predetermined threshold and output the result of the comparison.

Figure 2:
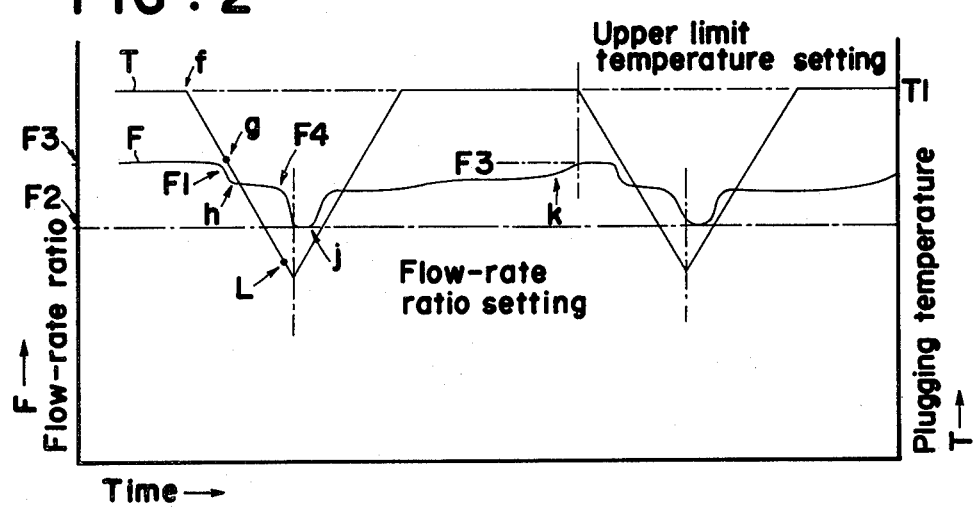
FIG. 2 is a graphical representation of the results of measurements performed by the apparatus of FIG. 1.

FIG. 2 shows an example of a measuring pattern of the measurement performed by the plugging meter in accordance with the invention. Hereinafter, the operation of the plugging meter will be described with reference to FIGS. 1 and 2.

The liquid sodium to be measured flows into the plugging meter through the inlet pipe 1, and is pumped by the electromagnetic pump 2. The liquid sodium then passes through the cooling passage and the by-pass passage in a divided flow, and is discharged through the outlet pipe 7.

Usually, the plugging orifice 10 is kept at a high temperature, before the measurement is commenced. Therefore, the liquid sodium can flow through the orifice 10 smoothly to allow the divider 14 to produce a large flow-rate ratio signal.

The temperature signal and the flow-rate ratio signal F are recorded by the recording device 19 which may be a pen recorder, for the time elapsed.

The flow-rate ratio setter 17 has been previously adjusted to set two flow-rate ratios, a minimum flow-rate ratio F2 and a resetting flow-rate ratio F3.

At the same time, the upper limit temperature setter 18 is set to provide a maximum sodium temperature T1 which is a temperature which causes a complete dissolution of the deposited substances at the plugging orifice 10.

In addition, the differentiation coefficients representative of the gradients of flow-rate ratio reductions for the first and the second pluggings are registered in the differentiation setter 20, so that respective plugging temperatures may be determined by means of the different gradients.

The automatic measurement is started at a point f in FIG. 2. The program signal generator 15 gradually lowers the level of its output, i.e. the reference signal S, with a pre-set gradient. Consequently, for the reasons as stated above, the temperature of the plugging orifice 10 is lowered.

The flow-rate ratio signal F is kept almost constant until a first plugging F1 takes place. Then, a mark as designated at g is provided on the temperature signal curve, by means of the marking means of the recording device 19, in accordance with the signal delivered from the differentiation setter 20, so as to display the first plugging temperature. This marking conveniently provides a readily visible representation of the temperature at which the reduction of the flow-rate ratio is commenced.

As the temperature of the plugging orifice is further decreased, after a period h of temporary lull or no plugging, a second plugging F4 takes place. At this moment, the marking means of the recording device dots a mark L on the temperature signal curve, in accordance with the signal delivered from the differentation setter 20.

As the level of the flow-rate ratio is further decreased and reaches a predetermined minimum level F2, the flow-rate ratio setter 17 is caused to deliver a signal C to the program signal generator 15 to control the operation of the latter, and the reference signal S from the program signal generator 15 starts to ascend with an optional gradient which is different from the gradient of the descending reference signal.

Consequently, the temperature of the plugging orifice is raised to cause an unplugging j. As the reference signal S is further increased and reaches the level T1 pre-set in the upper limit temperature setter 18, the setter 18 generates a signal to cause the signal generator 15 to maintain that level of the reference signal. Then, after an elapse of time, another unplugging k takes place, so that the flow-rate ratio signal F is restored to the resetting flow-rate ratio F3, thereby to complete one cycle of measurement.

When the flow-rate ratio signal F is restored to the level of the resetting flow-rate ratio F3, the flow-rate ratio setter 17 again produces a controlling signal C and supplies it to the program signal generator 15, so that the level of the reference signal S again starts to decrease to automatically turn to the next measurement cycle.

Although the gradient of change of the reference signal from the program signal generator may be optionally selected, it is to be noted that too large a gradient would reduce the reliability of the measurement, while too small a gradient would result in a too long a time for the completion of one cycle of measurement.

Therefore, the gradient should be suitably selected, taking the various conditions such as flow rate of the liquid sodium, constructions of the orifice and cooler, the scale of the apparatus and so on into account.

In the described embodiment, the temperature of the plugging orifice is raised by the flow of hot liquid sodium delivered from the main passage, while the operation of the cooler is stopped. However, the plugging meter of the invention may incorporate an electric heater 21a disposed in the vicinity of the flow passage in the cooler and a control 21 therefor adapted to be controlled by the output from the comparator 16. This type of control will provide a more accurate temperature rise of the plugging orifice, following a predetermined pattern of a program.

Although the invention has been described in its preferred form with a certain degree of particularity, it is understood that the present disclosure of the preferred form may have the details of construction and the combination and arrangement of parts change without departing from the spirit and the scope of the invention as hereinafter claimed.

What is claimed is:

1. In a plugging meter for measuring impurity concentration in a liquid metal and having a liquid metal inlet pipe provided with a first flow meter, a liquid metal outlet pipe, parallel passages connected between said liquid metal inlet and outlet pipes and including a cooling passage provided with cooling equipment and a by-pass passage, a second flow meter disposed in said cooling passage, a plugging orifice disposed in said cooling passage downstream from said cooling equipment and equipped with a temperature sensor, a divider adapted to divide the output from the second flow meter by the output from the first flow meter and produce a flow-rate ratio signal, and a recording device adapted to record said flow-rate ratio signal and the temperature signal delivered from said temperature sensor, the improvement which comprises a program signal generator adapted to transmit a reference signal for elevating and lowering the temperature of said plugging orifice with predetermined gradients, a comparator adapted to compare said reference signal with said temperature signal and to produce a temperature difference signal, and a flow-rate ratio setting device adapted to compare said flow-rate ratio signal with a signal representing a pre-set value and to produce a flow-rate ratio difference signal, the operation of said program signal generator being controlled by the flow-rate ratio difference signal from said flow-rate ratio setting device, and the operation of said cooling equipment being controlled by said temperature difference signal so as to control the temperature of said plugging orifice.

2. A plugging meter as claimed in claim 1, which further comprises a differentiation setter having a differentiation circuit and level comparators, said differentiation circuit being adapted to differentiate said flow-rate ratio signal, and said comparator being adapted to compare the differentiated value with a pre-set value and to generate a coincident signal when said differentiated value coincides with said pre-set value, whereby the plugging temperature is detected from the temperature signal at an instant when said coincident signal is generated.

3. A plugging meter as claimed in claim 1, which further comprises an upper limit temperature setter adapted to compare said temperature signal with a pre-set value and to control the operation of said program signal generator in accordance with the result of the comparison.

4. A plugging meter as claimed in claim 1, wherein said cooling equipment is a forced ventilation type having a damper, the degree of opening of said damper being controlled by said temperature difference signal transmitted from said comparator.

5. A plugging meter as claimed in claim 1, wherein said by-pass passage is provided with an orifice for restricting the flow of said liquid metal therethrough.

6. A plugging meter as claimed in claim 1, wherein said temperature sensor is constituted by a thermocouple.

7. A plugging meter as claimed in claim 1, which further comprises an electric heater disposed in the vicinity of said cooling passage, said electric heater being adapted to be controlled by said difference signal.

* * * * *